United States Patent [19]

Hunter et al.

[11] Patent Number: 5,314,446

[45] Date of Patent: May 24, 1994

[54] STERILIZED HETEROGENEOUS BRAIDS

[75] Inventors: Alastair W. Hunter, Bridgewater; Arthur Taylor, Jr., Plainfield, both of N.J.; Mark Steckel, Maineville, Ohio

[73] Assignee: Ethicon, Inc., Somerville, N.J.

[21] Appl. No.: 838,511

[22] Filed: Feb. 19, 1992

[51] Int. Cl.$^5$ ................................................. D04C 1/00
[52] U.S. Cl. ........................................ 606/231; 606/228; 87/7; 87/9; 428/370
[58] Field of Search .................. 606/228, 230, 231; 87/7, 8, 9; 428/225

[56] References Cited

U.S. PATENT DOCUMENTS

| | | | |
|---|---|---|---|
| 3,187,752 | 6/1965 | Glick | 128/335.5 |
| 3,463,158 | 8/1969 | Schmitt et al. | 606/228 |
| 3,527,650 | 9/1970 | Block | 117/7 |
| 3,636,956 | 1/1972 | Schneider | 128/335.5 |
| 3,942,532 | 3/1976 | Hunter et al. | 128/335.5 |
| 4,043,344 | 8/1977 | Landi et al. | 128/335.5 |
| 4,047,533 | 8/1977 | Perciaccante et al. | 128/335.5 |
| 4,052,988 | 10/1977 | Doddi et al. | 128/335.5 |
| 4,141,087 | 2/1979 | Shalaby et al. | 3/1 |
| 4,470,941 | 9/1984 | Kurtz | 264/136 |
| 4,624,256 | 11/1986 | Messier et al. | 128/335.5 |
| 4,946,467 | 8/1990 | Ohi et al. | 606/228 |
| 4,959,069 | 9/1990 | Brennan et al. | 606/228 |
| 4,979,956 | 12/1990 | Silverstrini | 623/13 |
| 5,116,360 | 5/1992 | Pinchuk et al. | 623/1 |
| 5,147,400 | 9/1992 | Kaplan et al. | 623/13 |

FOREIGN PATENT DOCUMENTS

| | | | |
|---|---|---|---|
| 2949920 | 3/1981 | Fed. Rep. of Germany | A61F 1/00 |
| WO86/00020 | 1/1986 | PCT Int'l Appl. | A61L 17/00 |
| 2082213 | 8/1980 | United Kingdom . | |
| 2218312A | 11/1989 | United Kingdom | A01K 91/00 |

Primary Examiner—George F. Lesmes
Assistant Examiner—Chris Raimund
Attorney, Agent, or Firm—Hal Brent Woodrow

[57] ABSTRACT

Heterogeneous braided multifilament of first and second set of yarns mechanically blended by braiding, in which first and second set of yarns are composed of different fiber-forming materials.

Heterogeneous braids are useful for preparation of surgical sutures and ligatures.

12 Claims, 3 Drawing Sheets

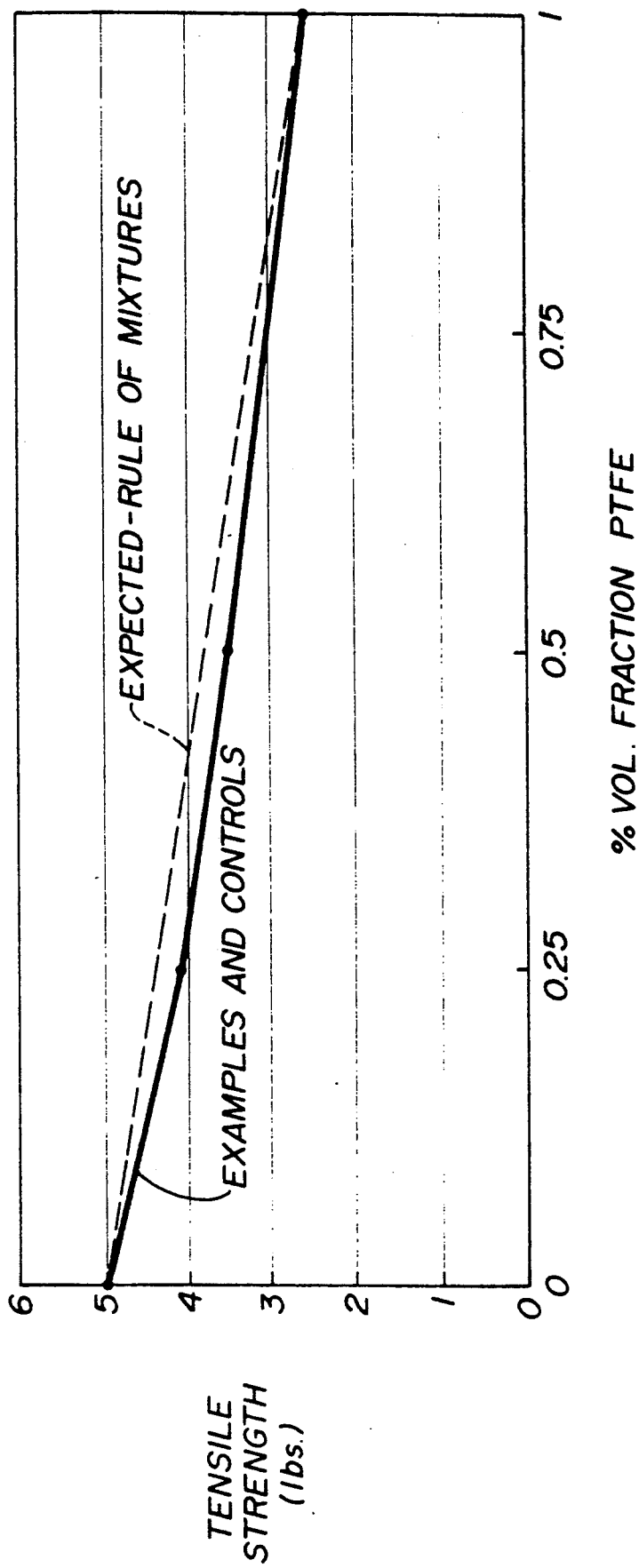

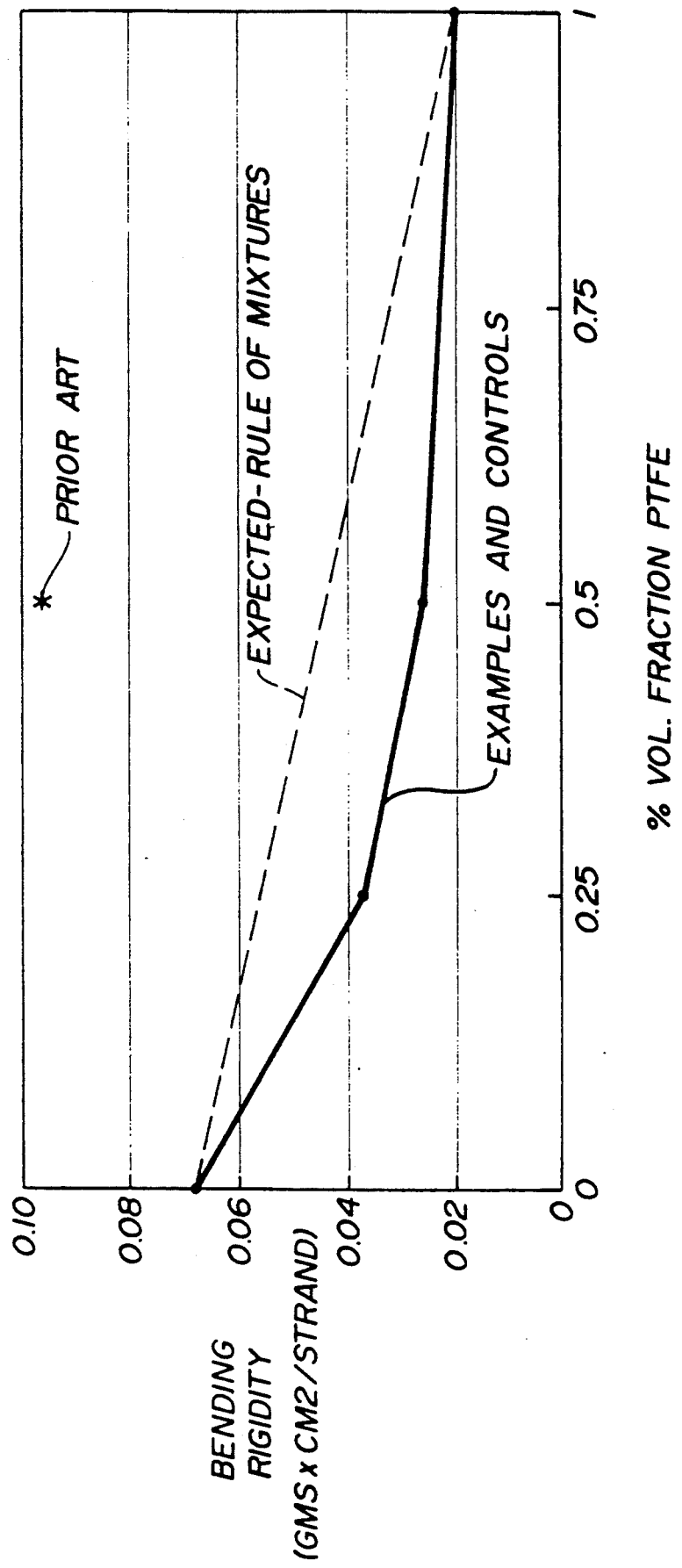

STERILIZED HETEROGENEOUS BRAIDS

BACKGROUND OF THE INVENTION

This invention relates to braided multifilaments, and especially to sterilized, braided multifilaments suitably adapted for use as surgical sutures or ligatures.

Braided multifilaments often offer a combination of enhanced pliability, knot security and tensile strength when compared to their monofilament counterparts. The enhanced pliability of a braided multifilament is a direct consequence of the lower resistance to bending of a bundle of very fine filaments relative to one large diameter monofilament. However, for this enhancement to be realized, the individual multifilaments must be able to bend unencumbered or unrestricted by their neighboring filaments. Any mechanism which reduces this individual fiber mobility, such as simple fiber-fiber friction, a coating which penetrates into the braid interstices, or a melted polymer matrix which adheres fibers together, will adversely affect braid pliability. In the extreme case where the multifilaments are entirely bonded together, the pliability or bending resistance closely approximates that of a monofilament.

Unfortunately, the prior art abounds with attempts to improve specific properties of multifilament braids at the expense of restricting the movement of adjacent filaments which make up the braid,. For example, multifilament sutures almost universally possess a surface coating to improve handling properties.

U.S. Pat. No. 3,942,532 discloses a polyester coating for multifilament sutures. The preferred polyester coating is polybutilate, which is the condensation product of 1,4-butanediol and adipic acid. U.S. Pat. No. 4,624,256 discloses a suture coating copolymer of at least 90 percent ϵ-caprolactone and a biodegradable monomer, and optionally a lubricating agent. Examples of monomers for biodegradable polymers disclosed include glycolic acid and glycolide, as well as other well known monomers typically used to prepare bioabsorbable coatings for multifilament sutures.

An alternative to the use of the commonly accepted coating compositions for multifilament sutures to improve handling properties is disclosed in U.S. Pat. 3,527,650. This patent discloses a coating composition of polytetrafluoroethylene (PTFE) particles in an acrylic latex. Although the PTFE particles act as an excellent lubricant to decrease the surface roughness of multifilament sutures, the particles have a tendency to flake off during use. Also, this particular coating is a thermoset which requires a curing step for proper application.

More recently, a dramatic attempt has been made to create a monofilament-like surface for a multifilament suture. U.S. Pat. No. 4,470,941 discloses the preparation of "composite" sutures derived from different synthetic polymers. The composite suture is composed of a core of low melting fibers around which are braided high melting fibers. Because of the lack of cohesiveness of the dissimilar fibers, the low melting fibers in the core are melted and redistributed throughout the matrix of the braided, high melting fibers. Although these composite sutures represent an attempt to combine the best properties of different synthetic fibers, it unfortunately fails in this respect due to increased stiffness (as evidenced by FIG. 3 which is described in detail below), apparently due to the reduction of fiber mobility resulting from the fusing of the fibers together.

Another attempt to enhance the properties of multifilament sutures can be found in WO 86/00020. This application discloses coating an elongated core of a synthetic polymer having a knot tenacity of at least 7 grams/denier with a film-forming surgical material. The film-forming surgical material can be absorbable or nonabsorbable, and can be coated on the elongated core by solution casting, melt coating or extrusion coating. Such coated multifilament sutures suffer from the same deficiencies which plague conventionally coated multifilament sutures.

All of the attempts described in the prior art to improve braid properties have overlooked the importance of fiber-fiber friction and its impact on fiber mobility and braid pliability. The properties of concern here include the fiber-fiber frictional coefficients (which frequently relate to the polymer's surface energy), the fiber cross-sectional shape and diameter, and the braid structure which influences the transverse forces across the braid. If fibers composed of highly lubricous polymers are used in the traditional manner, then a highly pliable braid can be prepared. However, in most cases, these braids will be relatively weak and unusable. Hence, a tradeoff between braid strength and pliability exists in the design of conventional braided multifilaments.

In view of the deficiencies of the prior art, it would be desirable to prepare multifilament sutures exhibiting improved pliability and handling properties. More specifically, it would be most desirable to prepare braided multifilaments composed of dissimilar fiber-forming materials in which the fiber-forming materials contribute significantly to enhanced pliability for the braided multifilament without appreciably sacrificing its physical properties.

SUMMARY OF THE INVENTION

The invention is a heterogeneous braid comprising a first and second set of continuous and discrete yarns in a sterilized, braided construction. At least one yarn from the first set is in direct intertwining contact with a yarn from the second set.

Each yarn from the first set is composed of a plurality of filaments of a first fiber-forming material, and each yarn from the second set is composed of a plurality of filaments of a second fiber-forming material.

Surprisingly, the heterogeneous braids may exhibit a combination of outstanding properties attributable to the specific properties of the dissimilar fiber-forming materials which make up the braided yarns. The dissimilar fiber forming materials do not require melt bonding or any other special processing techniques to prepare the heterogeneous braids of this invention. Instead, the integrity of the braid and therefore its properties is due entirely to the mechanical interlocking or weaving of the individual yarns. In fact, it is possible to tailor the physical and biological properties of the braid by varying the type and proportion of each of the dissimilar fiber forming materials used, as well as adjusting the specific configuration of the braid. For example, in preferred embodiments, the heterogeneous braid will exhibit improved pliability and handling properties relative to that of conventional homogeneous fiber braids, without sacrificing physical strength or knot security.

The sterilized, heterogeneous braids of this invention are useful as surgical sutures or ligatures, as well as for the preparation of any other medical device which would benefit from its outstanding physical or biological properties.

BRIEF DESCRIPTION OF THE DRAWINGS

FIG. 2 is a plot representing the relationship between the tensile strength of heterogeneous and homogeneous braids of polyethylene terephthalate (PET) and PTFE yarns, and the volume fraction of PTFE yarns in the braids; and FIG. 3 is a plot representing a relationship between the initial bending rigidity of heterogeneous and homogeneous braids of PET and PTFE yarns, and the volume fraction of PTFE yarns in the braids.

DETAILED DESCRIPTION OF THE INVENTION

Figure 1:
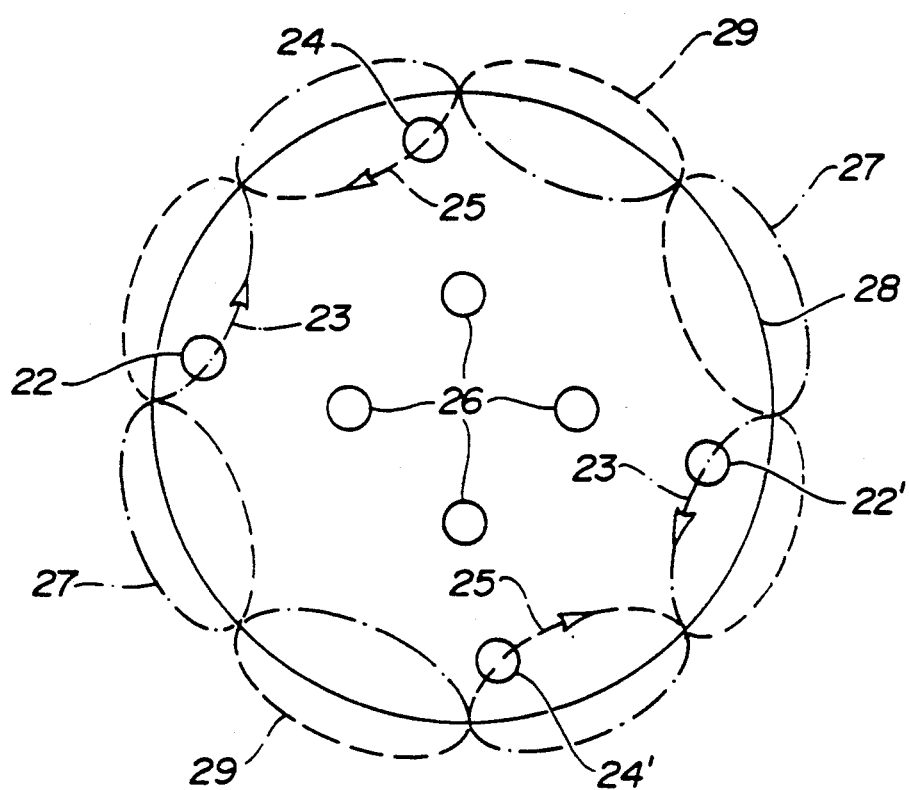
FIG. 1 illustrates a carrier layout for the preparation of a heterogeneous braid within the scope of this invention.

For purposes of describing this invention, a "heterogeneous" braid is a configuration composed of at least two sets of dissimilar yarns mechanically blended by intertwining the dissimilar yarns in a braided construction. The yarns are continuous and discrete, so therefore each yarn extends substantially along the entire length of the braid and maintains its individual integrity during braid preparation, processing and use.

The heterogeneous braids of this invention can be conventionally braided in a tubular sheath around a core of longitudinally extending yarns, although such a core may be excluded, if desired. Braided sheath sutures with central cores are shown in U.S. Pat. Nos. 3,187,752; 4,043,344; and 4,047,533, for example. A core may be advantageous because it can provide resistance to flattening, as well as increased strength. Alternatively, the braids of this invention can be woven in a spiral or spiroid braid, or a lattice braid, as described in U.S. Pat. Nos. 4,959,069 and 5,059,213.

The dissimilar yarns of the first and second set of yarns are braided in such a manner that at least one yarn from the first set is directly intertwined with, or entangled about, a yarn from the second set. Direct mechanical blending of individual, dissimilar yarns therefore occurs from the interweaving and interlocking of these dissimilar yarns, enhancing yarn compatibility and the overall physical and biological properties of the heterogeneous braid. Preferably, every yarn from the first set is in direct intertwining contact with a yarn of the second set to achieve the maximum degree of mechanical blending of the dissimilar yarns.

The first and second fiber-forming materials which make up the filaments of the first and second set of yarns, respectively, can be any materials capable of being spun into continuous filaments. Advantageously, the fiber-forming materials are nonmetallic.

The preferred fiber-forming materials are synthetic fiber-forming polymers which are melt or solution spun through a spinneret to prepare continuous filaments. The filaments so prepared are advantageously stretched to provide molecular orientation and annealed to enhance dimensional stability and/or biological performance. The fiber-forming polymers can be bioabsorbable or nonabsorbable, depending on the particular application desired. Examples of monomers from which bioabsorbable polymers are derived include, but are not limited to, some hydroxyacids and lactones, e.g. glycolic acid, lactic acid, glycolide, lactide, p-dioxanone, $\epsilon$-caprolactone and trimethylene carbonate, as well as copolymers and polymer blends derived from these monomers and others. Interestingly, numerous bioabsorbable heterogeneous braids exhibiting varying useful biological properties, such as breaking strength retention in vivo and the absorption profiles in vivo, can be prepared for specific applications by using different combinations of bioabsorbable polymers.

Preferably, the continuous filaments which make up the first and second set of yarns are derived from nonabsorbable polymers. In a preferred embodiment, the first set of yarns acts as lubricating yarns to improve the overall pliability, or compliance, and surface lubricity of the heterogeneous braid. Preferably, the fiber-forming material of the first set exhibits a surface energy (which frequently relates to surface lubricity) less than about 38 dyne/cm, as measured by contact angle of liquids on polymer surfaces, as described by Kissa, E., "Handbook of Fiber Science and Technology," Vol. II, Part B, Marcel Decker, 1984. Such fiber forming polymers include perfluorinated polymers, e.g. PTFE and fluorinated ethylene/propylene copolymers (FEP) and perfluoroalkoxy (PFA) polymers, as well as non-perfluorinated polymers such as polyvinylidene fluoride (PVDF), polyethylene/tetrafluorethylene copolymers (PETFE), the polycholorofluoroethylene polymers, polypropylene (PP) and polyethylene (PE). More preferably, the first fiber-forming material exhibits a surface energy less than about 30 dyne/cm. The preferred polymers for the first set are PTFE, PETFE, FEP, PE and PP, and the most preferred fiber forming polymer is PTFE.

In a more preferred embodiment, the lubricating yarns of the first set are mechanically blended with yarns of the second set which act to provide improved strength to the heterogeneous braid. Preferably, the second set of yarns exhibits a yarn tenacity greater than 3.0 grams/denier, more preferably greater than 5.0 grams denier. The preferred yarns are PET, nylon and aramid, and the most preferred yarns are PET.

In the most preferred embodiment, the heterogeneous braid is composed of a first set of PTFE yarns mechanically blended with a second set of PET yarns in a braided configuration. Advantageously, the braided sheath encloses a core of longitudinally extending PET yarns to further improve the overall strength and resistance to flattening of the heterogeneous braid. In this embodiment, the volume fraction of lubricating yarns in the braided sheath and core desirably ranges from about 20 to about 80 percent. A volume fraction of lubricating yarns below about 20 percent will not typically improve the pliability of the braid, and a volume fraction above about 80 percent may adversely affect the overall strength of the braid. The filament fineness for such a heterogeneous braid is preferably less than 10 denier per filament, preferably from about 0.5 to about 5 denier per filament. A more coarse filament may result in a stiffer braid. The preferred individual yarn denier is between 10 and 100 denier.

The heterogeneous braids of this invention can be prepared using conventional braiding technology and equipment commonly used in the textile industry, and in the medical industry for preparing multifilament sutures. For example, the first and second set of yarns can be interwoven as indicated by the plan view of the yarn carrier layout of FIG. 1 for the preparation of a braided multifilament. The individual yarns of the braided sheath feed from spools mounted on carriers 22, 22' and 24, 24'. The carriers move around the closed circular loop 28, moving alternately inside and outside the loop 28 to form the braiding pattern. One or more carriers are continually following a serpentine path in a first direction around the loop, while the remaining carriers are following a serpentine path in the other direction.

In the illustrated embodiment, carriers 22, 22' are travelling around serpentine path 27 in a clockwise direction as indicated by directional arrows 23, and carriers 24, 24' are travelling around serpentine path 29 in a counterclockwise direction as indicated by arrows 25. The moving carriers dispense yarns which intertwine to form the braid. The yarns from all the carriers in a constructed embodiment of FIG. 1 are dispensed upward with respect to the plane of the drawing, and the braid is taken up on a reel located above the plane of the drawing.

In one embodiment, moving carriers 22, 24 dispense yarns of the first set and moving carriers 22', 24' dispense yarns of the second set to form the heterogeneous braid. In a more preferred embodiment, moving carriers 22, 22' dispense yarns of the first set and moving carriers 24, 24' dispense yarns of the second set. This carrier layout provides a braid in which each yarn of the first set is directly intertwined with a yarn from the second set.

Advantageously, as illustrated in FIG. 1, disposed within the center of the loop 28 are carriers 26 which dispense the core yarns of the braid. In the most preferred embodiment of this invention, moving carriers 22, 22' dispense PTFE yarns, moving carriers 24, 24' dispense PET yarns, and core carriers 26 dispense PET yarns.

Numerous additional embodiments are contemplated within the scope of the invention using conventional braiding technology and equipment. For example, the carrier layout can be modified to prepare a braid configuration using from 3 to 28 sheath carriers, with or without any number of core yarns. Dissimilar yarns from the first and second set of yarns can be plied together using conventional techniques before braiding, and in this embodiment, the carriers can dispense identical bobbins of plied yarns composed of individual yarns from the first and second sets. This embodiment not only offers the advantage of inter-yarn mechanical blending, but also the intimate mixing associated with intra-yarn blending.

Similar to the preparation of conventional homogeneous braids, the yarns from which the heterogeneous braids are prepared are preferably nontextured. The yarn tension during braiding is advantageously adjusted so that the yarn elongation for each set of yarns is about equal. The equilibration of yarn elongation may prevent irregularities, for example, "core popping", which is the tendency of core yarns to break through the braided sheath as the braid is bent. The number of picks per inch in the finished braid can be adjusted to balance the tensile strength of the braid with braid quality, e.g. the tendency for core popping and overall braid smoothness.

After the heterogeneous braid is prepared, it is desirably scoured to remove machine oils and lubricants, and any foreign particles. The scoured braid is preferably stretched at a temperature between the glass transition temperature and melting temperature of the lower melting set of yarns. Therefore, the stretching temperature is such that none of the yarns is actually melted. The stretching operation densifies the braid and improves braid smoothness. Afterwards, the braid may be annealed while under restraint to improve dimensional stability, and in the case of absorbable braids, to improve the breaking strength retention in vivo.

If desired, the surface of the heterogeneous multifilament braid can be coated with a bioabsorbable or nonabsorbable coating to further improve the handleability and knot tiedown performance of the braid. For example, the braid can be immersed in a solution of a desired coating polymer in an organic solvent, and then dried to remove the solvent. Most preferably, the coating does not cause the fibers or yarns to adhere to one another increasing stiffness. However, if the surface of the heterogeneous braid is engineered to possess a significant fraction of the lubricous yarn system, the conventional coating may be eliminated saving expense as well as avoiding the associated braid stiffening.

If the surface of the braid is coated, than the coating composition may desirably contain bioactive materials such as antibiotics and growth factors.

The post-treated heterogeneous braid is sterilized so it can be used for a host of medical applications, especially for use as a surgical suture, preferably attached to a needle. The braid can be sterilized using any of the conventional techniques well known in the art. For example, sterilization can be effected by exposing the braid to gamma radiation from a cobalt 60 source. Alternatively, the braid can be sterilized by exposure to ethylene oxide.

In the following examples, the tensile properties and knot security are each determined using an Instron Tensile Tester. The tensile properties, i.e. the straight and knot tensile strength and the percent elongation, are determined generally according to the procedures described in U.S. Pat. No. 4,838,267. The knot security, which provides an indication as to the number of throws required to secure a knot so that it fails to slip before cleanly breaking, is measured by first tying a conventional square knot around a mandrel, pulling the knot apart on the Instron Tester to observe whether slipping occurs, and if so, then tieing knots with additional throws until 20 out of 20 knots break cleanly without slipping. The bending rigidity, which is the inverse of pliability, is determined using a Kawabata Pure Bending Tester, as discussed in "The Effects of Structure on the Geometric and Bending Properties of Small Diameter Braids", Drexel University Master Thesis, 1991, by Mr. E. Ritter.

The examples are illustrative only, and are not intended to limit the scope of the claimed invention. The types of yarns used to prepare the heterogeneous braid and the yarn geometry can be varied to prepare heterogeneous braids within the scope of the claimed invention which exhibit a combination of outstanding physical or biological properties.

EXAMPLES

Examples I and II describe heterogeneous braids of PTFE and PET yarns. In order to evaluate the relative performance of these braids, two controls are included which represent 100% PET and 100% PTFE braids, respectively. To the extent possible, the yarn materials and processing conditions are identical for the controls and heterogeneous braid examples. In addition, for comparison purposes, a braid is fabricated with identical materials but processed per the prior art U.S. Pat. No. 4,470,941.

CONTROL I

FIBER MATERIALS: An 8×0 PET braid is fabricated, i.e. 8 sheath yarns and 0 core yarns. All yarns are Dupont Dacron PET, 70 denier, 48 filament, type 52 yarn.

PROCESSING: The yarns are wound on braider bobbins per conventional methods, and the bobbins loaded on each carrier of a N.E. Butt 8 carrier braider. Machine settings include: 32 pick gear, 0.009" wire tension springs, and 183 rpm. The braid is aqueous scoured, and hot stretched at 30% draw ratio at 225° C.

CONTROL II

FIBER MATERIALS: An 8×0 PTFE braid is fabricated. All yarns are Dupont Teflon, 110 denier, 12 filament.

PROCESSING: The yarns are wound on braider bobbins per conventional methods, and the bobbins loaded on each carrier of a N.E. Butt 8 carrier braider. Machine settings include: 36 pick gear, no tension springs, and 183 rpm. The braid is scoured and hot stretched per the conditions described in CONTROL I.

EXAMPLE I

FIBER MATERIALS: An 8×0 heterogeneous braid is fabricated, consisting of four PET 70 denier yarns and four PTFE 110 denier yarns. The yarns are identical to that employed in CONTROL I and II. On a volume basis, the braid is 50.3% PET, and 49.7% PTFE.

PROCESSING: Four bobbins of PET yarn and four bobbins of PTFE yarn were wound by conventional means. The PET bobbins were loaded on the clockwise moving carriers of the N.E. Butt 8 carrier braider, and the PTFE yarn bobbins on the counter-clockwise moving carriers. Machine settings include: 32 pick gear, 0.009" tension springs on PET carriers, no springs on PTFE carriers, and 183 rpm. The braid is scoured and hot stretched per the conditions described in CONTROL I.

EXAMPLE II

FIBER MATERIALS: Identical to EXAMPLE I, except that 6 PET yarns and 2 PTFE yarns were used. On a volume basis, the braid is 75.5% PET, and 24.5% PTFE.

PROCESSING: Identical to EXAMPLE I, except that 2 PET bobbins replace 2 PTFE bobbins. All other braider machine settings, scour and hot-stretch conditions are identical to CONTROL I and II and EXAMPLE I.

PRIOR ART I

FIBER MATERIALS: Identical to EXAMPLE I. On a volume basis, the braid is 50.3% PET, and 49.7% PTFE.

PROCESSING: Identical to EXAMPLE I, except that the hot stretch temperature is at 300° C. and for a longer residence time to facilitate melting of the PET fibers.

The properties of CONTROLS I and II, and EXAMPLES I and II, and the PRIOR ART I are summarized in the following Table:

|  | USP DIAMETER (mils) | TENSILE STRENGTH (lbs) | KNOT STRENGTH (lbs) | BENDING RIGIDITY (gm × cm²) | KNOT STABILITY (# of throws) |
| --- | --- | --- | --- | --- | --- |
| CONTROL I | 10.68 | 4.98 | 3.14 | 0.0680 | 4 |
| CONTROL II | 9.11 | 2.58 | 2.04 | 0.0196 | 7 |
| EXAMPLE I | 9.71 | 3.55 | 2.41 | 0.0257 | 5 |
| EXAMPLE II | 10.35 | 4.10 | 2.67 | 0.0371 | 5 |
| PRIOR ART I | 8.81 |  |  | 0.0966 |  |

As may be expected, the tensile strengths of the heterogenous braid examples reflect the relative contributions of the individual components. This behavior is said to follow the "rule of mixtures", i.e. the composite property is a weighted average of the component properties. In equation form, $$P_c = (Vf_a)(P_a) + (Vf_b)(P_b)$$

where $P_c$ is a composite property (such as tensile strength or modulus), $P_a$ and $P_b$ are the properties of the components a and b, and $Vf_a$ and $Vf_b$ are the volume fractions of components a and b. This behavior is clearly observed in FIG. 2, which shows a plot of tensile strength versus volume fraction of PTFE yarns for the Examples and Controls, in relation to the expected plot according to the rule of mixtures.

Surprisingly, the bending rigidity of the heterogeneous braids in EXAMPLES I and II do not follow the rule of mixtures, and show an enhanced bending rigidity relative to the weighted average of its components. This is shown in FIG. 3 as a plot of bending rigidity versus %PTFE in the braids. Bending rigidity is the inverse of pliability, and is obtained by measuring the slope of the *bending moment-radius of curvature* plot of a suture strand in pure bending. Hence lower bending rigidity relates to a more pliable suture, which is a highly desirable property. The mechanism of this enhanced pliability is believed to be internal lubrication of the braid by the "solid lubricant" behavior of the low surface energy PTFE.

U.S. Pat. No. 4,470,941 discloses the preparation of a "composite" suture with a monofilament-like surface made from multifilament yarns. The composite suture is composed of two different synthetic polymer fibers, which is thermally processed to melt one of the fibers to form a continuous matrix. This process was utilized to produce the PRIOR ART I example, the data of which is shown in Table 1 and FIG. 3. It is observed that the melting of the PET fibers significantly increases the braid bending rigidity due to the bonding of the "non-melted" fibers together, hence resulting in a less pliable braid of diminished utility.

What is claimed is:

1. A surgical suture consisting essentially of a heterogeneous braid composed of a first and second set of continuous and discrete yarns in a sterilized, braided construction wherein at least one yarn from the first set is in direct intertwining contact with a yarn from the second set; and a) each yarn from the first set is composed of a plurality of filaments of a first fiber-forming material selected from the group consisting of PTFE, FEP, PFA, PVDF, PETFE, PP and PE; and
b) each yarn from the second set is composed of a plurality of filaments of a second fiber-forming material selected from the group consisting of PET, nylon and aramid; and
c) optionally a core.

2. The surgical suture of claim 1 wherein the suture is attached to a needle.

3. The surgical suture of claim 1 wherein the first fiber-forming material exhibits a surface energy less than about 38 dynes/cm.

4. The surgical suture of claim 3 wherein the first fiber-forming material exhibits a surface energy less than about 30 dynes/cm.

5. The surgical suture of claim 4 wherein the first set of yarns is PTFE.

6. The surgical suture of claim 5 wherein the second set of yarns exhibits a yarn tenacity greater than 3.0 grams/denier.

7. The surgical suture of claim 6 wherein the second set of yarns exhibits a yarn tenacity greater than 5.0 grams/denier.

8. The surgical suture of claim 1 wherein the second set of yarns is PET.

9. The surgical suture of claim 8 wherein the volume fraction of the first set of yarns in the braided sheath and core ranges from about 20 to about 80 percent.

10. The surgical suture of claim 9 wherein the fiber fineness of the yarns of the first and second sets is less than 10 denier per filament.

11. The surgical suture of claim 1 wherein at least one yarn from the first set of yarns is plied together to a yarn from the second set of yarns.

12. The surgical suture of claim 8 wherein the suture is attached to a needle.

* * * * *

(12) EX PARTE REEXAMINATION CERTIFICATE (6596th)
United States Patent
Hunter et al.

(10) Number: US 5,314,446 C1
(45) Certificate Issued: Jan. 6, 2009

(54) STERILIZED HETEROGENEOUS BRAIDS

(75) Inventors: Alastair W. Hunter, Bridgewater, NJ (US); Arthur Taylor, Jr., Plainfield, NJ (US); Mark Steckel, Maineville, OH (US)

(73) Assignee: Ethicon, Inc., New Brunswick, NJ (US)

Reexamination Request:
No. 90/008,975, Dec. 21, 2007

Reexamination Certificate for:
Patent No.: 5,314,446
Issued: May 24, 1994
Appl. No.: 07/838,511
Filed: Feb. 19, 1992

(51) Int. Cl.
*D04C 1/00* (2006.01)

(52) U.S. Cl. .............................. 606/231; 606/228; 87/7; 87/9; 428/370

(58) Field of Classification Search ......................... None
See application file for complete search history.

(56) References Cited

U.S. PATENT DOCUMENTS

| | | | |
|---|---|---|---|
| 3,359,983 A | 12/1967 | Northey | 128/335.5 |
| 3,454,011 A | 7/1969 | Wagner | 128/335.5 |
| 3,939,969 A | 2/1976 | Miller et al. | 206/63.3 |
| 3,942,532 A | 3/1976 | Hunter et al. | 128/335.5 |
| 4,060,885 A | 12/1977 | Hoffman et al. | 29/407 |
| 4,142,628 A | 3/1979 | Marocco et al. | 206/63.3 |
| 4,183,431 A | 1/1980 | Schmidt et al. | |
| 4,543,286 A | 9/1985 | Harpell et al. | 428/288 |
| 4,563,392 A | 1/1986 | Harpell et al. | 428/394 |
| 4,610,688 A | 9/1986 | Silvestrini et al. | |
| 4,950,285 A | 8/1990 | Wilk | 606/232 |
| 4,967,902 A | 11/1990 | Sobel et al. | 206/63.3 |
| 5,080,667 A | 1/1992 | Chen et al. | 606/227 |
| 5,120,802 A | 6/1992 | Mares et al. | |
| 5,123,913 A | 6/1992 | Wilk et al. | 606/232 |
| 5,147,400 A | 9/1992 | Kaplan et al. | 623/13 |
| 5,217,495 A | 6/1993 | Kaplan et al. | 623/13 |
| 5,234,006 A | 8/1993 | Eaton et al. | 128/898 |
| 5,318,575 A | 6/1994 | Chesterfield et al. | 606/151 |
| 5,662,682 A | 9/1997 | Chesterfield et al. | 606/228 |

FOREIGN PATENT DOCUMENTS

| | | |
|---|---|---|
| EP | 0485986 A1 | 5/1992 |
| GB | 2 218 312 | 11/1989 |
| GB | 2 218 312 A | 11/1989 |

OTHER PUBLICATIONS

Dyneema SK60, High strength/high modulus fiber, Properties & Applications, DSM Brochure, 1987.

Cohan, B. et al., "An Evaluation of Ultrastrong Polyethylene Fiber as an Ophthalmic Structure", Arch Opthalmol, vol. 103, Dec. 1985.

In the United States District Court for the District of Massachusetts, *DePuy Mitek, Inc.*, v. *Arthrex, Inc. and Pearsalls Ltd.*, Civil Action # 04–12457–PBS, Memorandum and Order, Jan. 31, 2007, 20 pages.

In the United States District Court for the District of Massachusetts, *DePuy Mitek, Inc.*, v. *Arthrex, Inc.*, Civil Action # 04–12457–PBS, Defendants Arthrex, Inc.'s and Pearsalls, Ltd.'s Motion for Summary Judgment, Document 39, Aug. 11, 2006, 4 pages.

In the United States District Court for the District of Massachusetts, *DePuy Mitek, Inc.*, v. *Arthrex, Inc.*, Civil Action # 04–12457–PBS, Memorandum in Support of Defendants Arthrex, Inc.'s and Pearsalls, Ltd.'s Motion for Summary Judgment wuth Attached Exhibits 1 thru 45, Document 40, Aug. 11, 2006.

(Continued)

*Primary Examiner*—Catherine S. Williams

(57) ABSTRACT

Heterogeneous braided multifilament of first and second set of yarns mechanically blended by braiding, in which first and second set of yarns are composed of different fiber-forming materials.

Heterogeneous braids are useful for preparation of surgical sutures and ligatures.

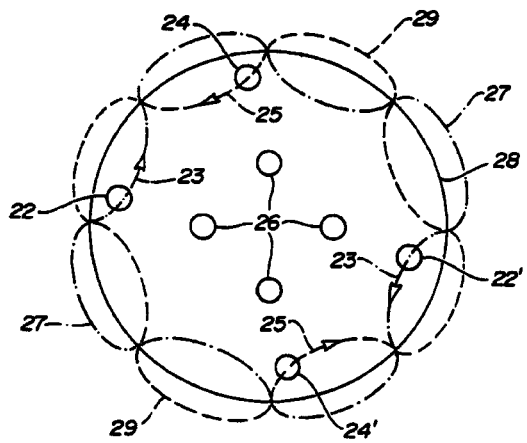

OTHER PUBLICATIONS

In the United States District Court for the District of Massachusetts, *DePuy Mitek, Inc., v. Arthrex, Inc.*, Civil Action # 04–12457–PBS, Defendants Arthrex, Inc.'s and Pearsalls, Ltd.'s Concise Statement of Material Facts in Support of Their Motion for Summary Judgment, Document 42, Aug. 11, 2006, 11 pages.

In the United States District Court for the District of Massachusetts, *DePuy Mitek, Inc., v. Arthrex, Inc., and Pearsalls Ltd.*, Civil Action # 04–12457–PBS, DePuy Mitek's Memorandum in Opposition to Arthrex's Motion for Summary Judgment, Sep. 1, 2006, Document 60, 37 pages.

In the United States District Court for the District of Massachusetts, *DePuy Mitek, Inc., v. Arthrex, Inc., and Pearsalls Ltd.*, Civil Action # 04–12457–PBS, DePuy Mitek's Response to Defendants Arthrex, Inc.'s and Pearsalls, Ltd.'s Concise Statement of Material Facts in Support of their Motion for Summary Judgment of Infringement, 40 pages, with attached Exhibits, Document #63, Sep. 1, 2006.

In the United States District Court for the District of Massachusetts, *DePuy Mitek, Inc., v. Arthrex, Inc.*, Civil Action # 04–12457–PBS, Defendants Arthrex, Inc.'s and Pearsalls, Ltd.'s Reply Memorandum in Support of their Motion for Summary Judgment, Document # 73, Sep. 15, 2006.

In the United States District Court for the District of Massachusetts, *DePuy Mitek, Inc., v. Arthrex, Inc.*, Civil Action # 04–12457–PBS, Defendants' Reply to Miteks's Facts Submitted in Response to Arthrex's Summary Judgment Motion, Document #74, Sep. 15, 2006.

In the United States District Court for the District of Massachusetts, *DePuy Mitek, Inc., v. Arthrex, Inc., and Pearsalls, Ltd.*, Civil Action # 04–12457–PBS, Expert Report of Dr. Matthew Hermes, Mar. 24, 2006, 72 pages.

In the United States District Court for the District of Massachusetts, *DePuy Mitek, Inc., v. Arthrex, Inc.*, Civil Action # 04–12457–PBS, Expert Report of Dr. Debi Prasad Mukherjee Concerning Invalidity of U.S. Patent No. 5,314,446, Mar. 3, 2006, 33 pages.

In the United States District Court for the District of Massachusetts, *DePuy Mitek, Inc., v. Arthrex, Inc.*, Civil Action # 04–12457–PBS, Arthrex, Inc.'s Answer and Counterclaim in Response to Depuy Mitek, Inc.'s Complaint, Dec. 13, 2004, 6 pages.

In the United States District Court for the District of Massachusetts, *DePuy Mitek, Inc., v. Arthrex, Inc.*, Civil Action # 04–12457–PBS, Arthrex, Inc.'s Answer and Counterclaim in Response to Depuy Mitek, Inc.'s Amended Complaint, Sep. 26, 2005, 8 pages.

In the United States District Court for the District of Massachusetts, *DePuy Mitek, Inc., v. Arthrex, Inc.*, Civil Action # 04–12457–PBS, Pearsalls Limited's Answer and Counterclaim in Response to Depuy Mitek, Inc.'s Amended Complaint, Oct. 14, 2005, 8 pages.

In the United States District Court for the District of Massachusetts, *DePuy Mitek, Inc., v. Arthrex, Inc., and Pearsalls Ltd.*, Civil Action # 04–12457–PBS, DePuy Mitek's Motion for Summary Judgment of Infringement and No Inequitable Conduct, Aug. 11, 2006, Document #36.

In the United States District Court for the District of Massachusetts, *DePuy Mitek, Inc., v. Arthrex, Inc., and Pearsalls Ltd.*, Civil Action # 04–12457–PBS, DePuy Mitek's Statement of Undisputed Material Facts in Support of Its Motion for Summary Judgment of Infringement and No Inequitable Conduct, Aug. 11, 2006, Document 38.

In the United States District Court for the District of Massachusetts, *DePuy Mitek, Inc., v. Arthrex, Inc.*, Civil Action # 04–12457–PBS, Defendants' Opposition to Depuy Mitek's Motion for Summary Judgment of Infringement and No Inequitable Conduct, Sep. 1, 2006, Document 61.

In the United States District Court for the District of Massachusetts, *DePuy Mitek, Inc., v. Arthrex, Inc.*, Civil Action # 04–12457–PBS, Defendants' Responses to Depuy Mitek's Statement of Undisputed Material Facts in Support of Its Motion for Summary Judgment of Infringement and No Inequitable Conduct, Sep. 1, 2006, Document 62.

In the United States District Court for the District of Massachusetts, *DePuy Mitek, Inc., v. Arthrex, Inc., and Pearsalls Ltd.*, Civil Action # 04–12457, Mitek's Reply in Support of its Motion for Summary Judgment of Infringement and No Inequitable Conduct, Sep. 15, 2006, Document 72.

In the United States District Court for the District of Massachusetts, *DePuy Mitek, Inc., v. Arthrex, Inc., and Pearsalls Ltd.*, Civil Action # 04–12457, DePuy Mitek's Reply to Defendants' Responses to DePuy Mitek's Statement of Undisputed Material Facts in Support of Its Motion for Summary Judgment of Infringement and No Inequitable Conduct, Sep. 15, 2006, Document 66.

In the United States District Court for the District of Massachusetts, *DePuy Mitek, Inc., v. Arthrex, Inc.*, Civil Action # 04–12457, Deposition of Dr. Mark G. Steckel, Jan. 26, 2006.

In the United States District Court for the District of Massachusetts, *DePuy Mitek, Inc., v. Arthrex, Inc., Day II*, Civil Action # 04–12457, Deposition of Dr. Mark. G. Steckel, Feb. 3, 2006.

In the United States District Court for the District of Massachusetts, *DePuy Mitek, Inc., v. Arthrex, Inc.*, Civil Action # 04–12457, Deposition of Dr. David S. Brookstein, Jul. 26, 2006.

In the United States District Court for the District of Massachusetts, *DePuy Mitek, Inc., v. Arthrex, Inc.*, Civil Action # 04–12457, Deposition of Dr. David S. Brookstein, Day 2, Jul. 27, 2006.

In the United States District Court for the District of Massachusetts, *DePuy Mitek, Inc., v. Arthrex, Inc.*, Civil Action # 04–12457, Deposition of Dr. Matthew Hermes, Jul. 27, 2006.

In the United States District Court for the District of Massachusetts, *DePuy Mitek, Inc., v. Arthrex, Inc.*, Civil Action # 04–12457, Deposition of Debi Prasad Mukherjee, Jun. 13, 2006.

In the United States District Court for the District of Massachusetts, *DePuy Mitek, Inc., v. Arthrex, Inc.*, Civil Action # 04–12457, Deposition of Debi Prasad Mukherjee, vol. II, Jun. 14, 2006.

In the United States District Court for the District of Massachusetts, *DePuy Mitek, Inc., v. Arthrex, Inc.*, Civil Action # 04–12457, Pearsalls Limited's Objections and Answers to Depuy Mitek, Inc.'s First Set of Interrogatories to Pearsalls Limited, Jan. 27, 2006, 25 pages.

In the United States District Court for the District of Massachusetts, *DePuy Mitek, Inc., v. Arthrex, Inc.,* Civil Action # 04–12457, Arthrex, Inc.'s Supplemental Objections and Responses to Depuy Mitek, Inc.'s Interrogatory Nos. 2,4,10 and 12, Apr. 2005, 11 pages.

In the United States District Court for the District of Massachusetts, *DePuy Mitek, Inc., v. Arthrex, Inc.,* Civil Action # 04–12457, Arthrex, Inc.'s Second Supplemental Objections and Responses to Depuy Mitek, Inc's Interrogatory Nos. 3,5, and 7 and Arthrex's Supplemental Objections and Response to Depuy Mitek's Inc.'s Interrogatory No. 6, Jan. 27, 2006, 11 pages.

Cohan, B. E. et al., "An Evaluation of Ultrastrong Polyethylene Fiber as an Ophthalmic Suture", *Arch Ophthalmol,* Dec. 1985, 103, 1816–1821.

Dyneema SK60, High Strength/High Modulus Fiber, Properties and Applications, 1987, DSM of the Netherlands, 10 pages, PR–08420–PR08429.

In the United States District Court for the District of Massachusetts, *DePuy Mitek, Inc., v. Arthrex, Inc.,* Civil Action # 04–12457, Deposition of Hal Brent Woodrow, Nov. 2, 2005.

In the United States District Court for the District of Massachusetts, *DePuy Mitek, Inc., v. Arthrex, Inc.,* Civil Action # 04–12457, Deposition of Matthew Goodwin, Jan. 17, 2006.

In the United States District Court for the District of Massachusetts, *DePuy Mitek, Inc., v. Arthrex, Inc.,* Civil Action # 04–12457, Deposition of E. Richard Skula, Feb. 10, 2006.

In the United States District Court for the District of Massachusetts, *DePuy Mitek, Inc., v. Arthrex, Inc.,* Civil Action # 04–12457, DePuy Mitek's Memorandum Relating to Patent Ownership, Aug. 2, 2007, Document 149.

In the United States District Court for the District of Massachusetts, *DePuy Mitek, Inc., v. Arthrex, Inc.,* Civil Action # 04–12457, Defendants Arthrex, Inc.'s and Pearsalls, Ltd.'s Memorandum Relating to Patent Ownership, Aug. 7, 2007, Document 156.

In the United States District Court for the District of Massachusetts, *DePuy Mitek, Inc., v. Arthrex, Inc.,* Civil Action # 04–12457, Defendants Arthrex Inc.'s and Pearsalls, Ltd.'s Supplemental Memorandum Relating to Patent Ownership, Aug. 9, 2009, Document 160.

In the United States District Court for the District of Massachusetts, *DePuy Mitek, Inc., v. Arthrex, Inc.,* Civil Action # 04–12457, DePuy Mitek's Supplemental Memorandum in Support of Its Ownership of the Hunter 446 Patent, Aug. 9, 2007, Document 158.

In the United States District Court for the District of Massachusetts, *DePuy Mitek, Inc., v. Arthrex, Inc.,* Civil Action # 04–12457, Defendants Arthrex, Inc.'s and Pearsalls, Ltd.'s Second Supplemental Memorandum Relating to Patent Ownership, Aug. 12, 2007, Document 162.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1, 2, 8, 9 and 12 is confirmed.

Claims 3–7, 10 and 11 were not reexamined.

\* \* \* \* \*